United States Patent [19]
Chatenever

[11] Patent Number: 4,722,000
[45] Date of Patent: Jan. 26, 1988

[54] ADAPTER FOR ENDOSCOPIC CAMERA

[75] Inventor: David Chatenever, Santa Barbara, Calif.

[73] Assignee: Medical Concepts Incorporated, Santa Barbara, Calif.

[21] Appl. No.: 914,055

[22] Filed: Oct. 1, 1986

[51] Int. Cl.$^4$ ............................................. H04N 7/18
[52] U.S. Cl. .................................... 358/98; 358/229; 350/558; 128/6
[58] Field of Search .................. 358/98, 100, 99, 225, 358/229; 350/588; 128/4, 6

[56] References Cited

U.S. PATENT DOCUMENTS

| | | | |
|---|---|---|---|
| 4,076,018 | 2/1978 | Heckele | 128/6 |
| 4,279,246 | 7/1981 | Chikama | 350/588 X |
| 4,344,092 | 8/1982 | Miller | 358/98 X |
| 4,355,861 | 10/1982 | Scbald | 358/229 X |
| 4,413,278 | 11/1983 | Feinbloom | 358/98 X |
| 4,414,576 | 11/1983 | Randmae | 358/229 |
| 4,439,030 | 3/1984 | Ueda | 358/98 X |
| 4,621,618 | 11/1986 | Omagari | 358/98 X |
| 4,639,772 | 1/1987 | Sluyter | 358/98 |

FOREIGN PATENT DOCUMENTS 0211134 12/1983 Japan ...................................... 358/98

*Primary Examiner*—Howard W. Britton
*Assistant Examiner*—Victor R. Kostak
*Attorney, Agent, or Firm*—Elliott N. Kramsky

[57] ABSTRACT

An adapter for coupling an endoscope to a camera head. A front window assembly includes a cup-like element for insertion within the chassis of the adapter. A plurality of resistive heating elements is mounted to an annular printed circuit board that is fitted within the cup-like element. The resistive elements are energized by the camera power source to heat the adjacent front window of the adapter. Radial heating of the window raises the moisture-pressure gradient of its surface above that of adjacent metal surfaces, eliminating condensation from the surface of the window.

20 Claims, 3 Drawing Figures

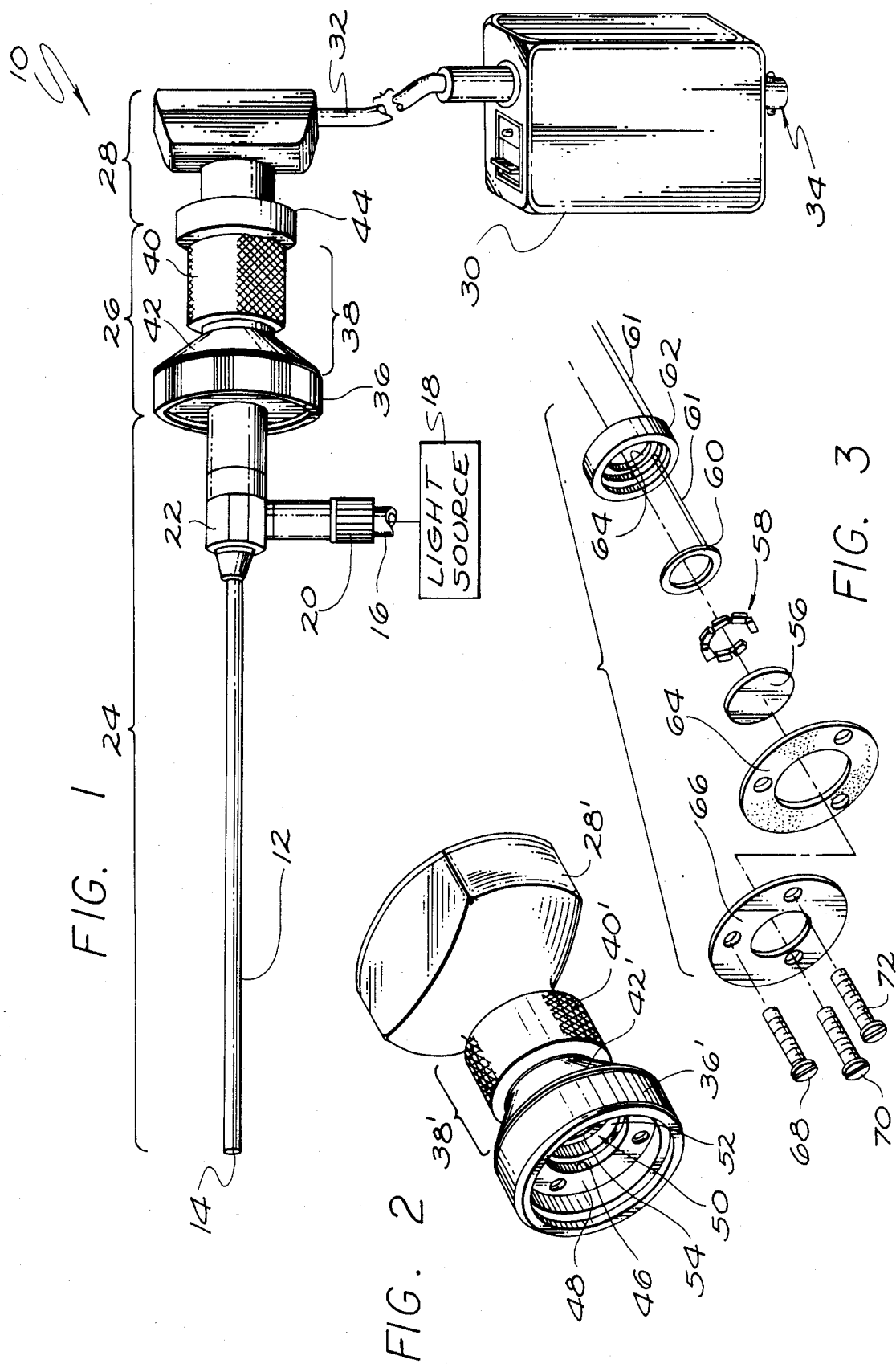

ADAPTER FOR ENDOSCOPIC CAMERA

BACKGROUND

1. Field of the Invention

The present invention relates to apparatus for use in association with endoscopic medical video equipment. More particularly, this invention pertains to an improved endoscopic adapter.

2. Description of the Prior Art

The advent of various endoscopic instruments has proven to be a significant aid to both diagnosis and the performance of surgical procedures. This instrument comprises an elongated probe for penetration and viewing of otherwise-inaccessible body regions. Examples of endoscopic instruments include the laparascope, cystoscope, arthroscope, bronchoscope, colonoscope, etc. the functions and areas of use of which are apparent from the nomenclature.

The probe may be either flexible or rigid in accordance with its intended application. The physician is able to view the body region adjacent to the distal end of the probe through an eyepiece near the proximal end.

While providing a substantial technical advance, the utility of the endoscope has been significantly increased by the development of video cameras for coupling to the image output of the endoscope. The use of such a camera protects the vision of the physician in those instances in which a highly-reflective medium must be viewed with bright illumination. This often occurs in orthoscopic surgery where high intensity illumination of reflective bone tissue can cause injury to the retina of an operating physician.

The combination of video camera with the endoscope, as opposed to direct viewing, promotes the operator comfort and, hence, instrument utility. When using a camera, the physician needn't position himself throughout the examination to accommodate an eyepiece located near the proximal end of the endoscope. An assistant may hold and position the endoscope while the operating physician's hands are freed to manipulate the surgical tools. As the physician and his assistant may view the image at the same time on a common monitor, prompt and accurate movement of the scope is assured throughout the operation. Thus tissue trauma due to movements of the scope is lessened.

Finally, the incorporation of a video camera permits both recordation and real time transmission of procedures. This opens many possibilties not offered by conventional endoscopy including real time consultations (and teaching) from distant venues and significant documentation benefits.

The adaptation of video camera technology to endoscopic imaging requires a means for adapting the conventional endoscope to a video camera head. Conventional apparatus for this purpose include a mechanism for grasping the endoscope that is, in turn, coupled at its opposed end to the camera head. Viewing optics mounted within a sleeve are movable within an internal bore for focusing purposes. Means are provided in association with the adapter for focusing the optics.

A window is located the front or endoscope end of the adapter. Since the system is almost always employed within a critical environment, the entire system must be sterilized before use. This involves immersion of the equipment in a sterile bath for about fifteen minutes, followed by drying and assembly.

Viewing clarity is, of course, essential to the physician. This is often hampered during use by the presence of condensation on the front window of the adapter. This condensation results from the unavoidable presence of minute amounts of liquid on the surfaces of the adapter. Light energy that is coupled into the endoscope for illumination during operation heats the metallic portions of the instrument more than the glass window. As a result, some condensation generally takes place on the relatively cool front window which offers a lower moisture-pressure than the surrounding metal surfaces.

The resulting reduction in clarity can significantly hinder the physician's diagnostic ability. Alternatively, reduced clarity can limit the physician's ability to perform necessary procedures.

SUMMARY

The foregoing and other shortcomings of the prior art are addressed and overcome by the present invention that provides an adapter for use with an endoscope. The adapter includes means for coupling to the endoscope. Means are provided for transmitting a focused image of the distal end of the endoscope to a camera head. A window is arranged adjacent to the means for coupling. Finally, means are provided for heating the window.

The foregoing features and advantages of the invention will become clearer from the detailed description that follows. Such description is accompanied by a set of illustrative drawing figures. The drawing figures and the written description include numerals that point to the various features of this invention, like numerals referring to like features throughout both the written description and the drawings.

BRIEF DESCRIPTION OF THE DRAWINGS

FIG. 1 illustrates the principal elements of an endoscopic system for employing the teachings of the invention;

FIG. 2 is a perspective view of a portion of a camera head-and-endoscopic adapter arrangement for receiving condensation removal apparatus in accordance with the invention; and FIG. 3 is an exploded perspective view of apparatus for prevention and removal of condensation from the front window of an endoscopic adapter in accordance with the invention.

DETAILED DESCRIPTION

Turning now to the drawings, an endoscopic system 10 for employing the teachings of the invention is illustrated in FIG. 1. Such a system includes a probe 12 for insertion into either an antomical cavity or an incision. A window 14 is provided at the distal end of the probe 12. The window 14 admits an illuminated view of the adjacent anatomy that is transmitted through optics to the opposed proximal end of the probe 12 without noticeable degradation.

Illumination enters the probe 12 through a light guide 16 that accepts the output of a light source 18. A tightening ring 20 is provided at the end of the guide 16 to permit the transmitted light to be coupled into the probe 12 through the body 22 of the endoscope 24.

The probe 12 is the only portion of the system 10 that actually enters the body. It may be of either rigid stainless steel or flexible optical fiber construction and possesses various dimensions in accordance with the intended use. For example, rigid constructions may range from six (6) inches to a couple of feet in length and from less than 2 to twelve (12) millimeters in diameter. Arthroscopy joint surgery generally requires a rigid probe having a diameter of about four (4) millimeters while much larger diameter probes are utilized for laparoscopy (abdominal cavity surgery). Upper and lower g.i. procedures require flexible probes. Bronchoscopes are generally at the lower end of the diameter scale while upper g.i. scopes for esophegeal and stomach procedures fall into the ten-to-twelve millimeter range. Twelve millimeter diameter colonscopes of about one and one-half meters in length are used for lower g.i. procedures.

In an "ordinary" application of the endoscope (i.e. without video camera) an eyecup and focusing lens arrangement is located at the end opposite the probe end of the body 22. However, in a conventional medical video arrangement, the lens system is associated with an adapter 26 for coupling the image output of the endoscope 24 into a video camera head 28 that is, in turn, electrically connected to a camera processor 30 by means of a conductor 32.

The focussed image which emerges from the adapter 26 is detected by a pickup device, such as a CCD sensor, within the camera head 28. The camera head 28 additionally includes preamplifier, line driving and receiving circuitry for communicating with the camera processor 30. The pixels of the CCD sensor are read out under processor control, digitized and stored therein. An output port 34 is provided for inserting either a video monitor(s) or recording apparatus.

Returning to the adapter 26, such apparatus generally includes a grasping mechanism 36, chassis 38 and focusing ring 40. The grasping mechanism 36 is designed to engage the adapter 26 to the body of the endoscope 24. The chassis 38 which terminates in a flared segment 42 has an internal bore. The system's focusing optics, fitted within a metal sleeve, are axially movable within the bore in response to rotation of the focusing ring 40. The front window of the adapter (not shown in FIG. 1) is fitted within the flared segment 42.

As shown in FIG. 1, the camera head 28 is separate from the adapter 26. The head 28 includes a conventional "C" mount 44. The end of the adapter 26 is arranged so that the adapter readily interlocks with the camera head. The teachings of this invention are equally applicable to an endoscopic system wherein the adapter and camera head form an integral unit.

FIG. 2 is a perspective view of a portion of an integral camera head-and-endoscopic adapter arrangement in accordance with the invention. As mentioned in the foregoing paragraph, this arrangement and that of the preceding figure are interchangeable insofar as the teachings of the invention. Corresponding parts of the two arrangements are given a primed notation in the current figure.

As can be seen in this view, the ring-like portion of the grasping mechanism 36' is somewhat cup-shaped with a circular central aperture 46 in the bottom 48 thereof. The aperture is aligned with and forms a portion of the bore that runs through the interior of the adapter 26.

The internal aperture 50 of the otherwise-solid flared segment 42' forms the portion of the bore adjacent the aperture 46 discussed above. As can be seen, the aperture 50 comprises sections 52 and 54 of differing diameters, the rear section 54 being of lesser size. As will become apparent, the shoulder formed therebetween acts as a stop for securing a front window mount within the flared segment 42'.

FIG. 3 is an exploded perspective view of a front window mount including apparatus for preventing and/or removing condensation and thus clarifying the view of the physician in accordance with this invention. The window 56 is formed of an optical quality glass of about one millimeter thickness and coated for good transmission. In the prior art, such window was simply glued onto the end of the adapter 26 adjacent the metallic (mostly aluminum) structures discussed above. As mentioned above, the glass of the window and the surrounding metal structures necessarily form a closed system wherein the surrounding surfaces presented higher moisture-pressure gradients as a consequence of the conduction of heat from the entering illumination. As a result, traces of liquid condensed onto the window 56, obscuring the physician's view, during the instrument's operation.

In accordance with the invention, apparatus is provided for overcoming this common phenomenon of the prior art by applying heat in such a way that the above described process will not produce condensation on the window. Such heat is applied radially from the periphery of the window 56 whereby its effects increase additively toward the center. As the effect of heating the window is to raise the moisture-pressure gradient of such surface (above that of the surrounding metal surfaces), the removal (or absence) of condensation will take place more readily as one moves toward the widow's center. As a consequence, the most critical portion of the physician's view is most reliably unclouded by condensation.

The heating elements of the system comprise a "wagon train" arrangement of seven (or other plurality of) surface mount resistors 58. The resistors are connected in parallel by means of plated throughholes that connect mounting pads with interconnect patterns on either side of an annular double sided printed circuit board 60. In the event that seven resistors are utilized, appropriate components could comprise 3.9 kilohm, one-eighth watt rated resistors commercially available under product designation CR 21 from Kyocera International of San Diego. The printed circuit board 60 can be fabricated of fiberglass or other standard p. c. board laminate.

Conductors 61 connect the resistive heating circuitry described above to the camera power source. The conductors are glued to the inside of the bore that runs through the adapter 26 to avoid interference with the physician's view. In the event that an adapter unit is employed that is separate from the camera head, a conventional mechanical connection scheme may be employed that provides a conductive path between the resistive heating elements and the camera power source when the adapter and the camera head are mechanically coupled.

The conductors 61 pass through a small opening in the bottom of a cup-like element 62. The element is formed of an appropriate elastomeric material such as for providing thermal insulation between the window 56 and the surrounding metallic assemblies. The elastomeric material sold under the trademark "Delrin" is an appropriate material for the element 62.

An opening 64 exists in the bottom of the 62 provides a stop for maintaining the position of the p.c.b. 60 (with resistor array 58 mounted thereon) within the dimensionally-matching rear cavity. The diameter of the interior is increased toward the front of the element 62 whereby a somewhat larger cavity is formed to accept the widow 56. The outside diameter of the element 62 is such that the element fits within the larger diameter bore that is interior to the flared segment 42' while its height is equal to the height of the cavity formed therein. Thus, the front window arrangement is flush with the front surface of the flared segment 42' when assembled.

The arrangement is sealed within the flared element 42' by means of a gasket 64 of elastomeric material. The inner diameter of the gasket 64 is slightly smaller than that of the window 56 while its outer diameter is equal to the outside diameter of the flared segment 42'. A metal ring 66 of identical dimension overlies the annular elastomeric ring 64 and screws 68, 70 and 72 are provided for sealably securing the entire front window mount assembly within the flared segment 42'.

The foregoing arrangement permits the window to be sealably secured without the use of glue. Such glue is subject to weakening over time as a result of the caustic nature of the sterilizing solutions commonly employed for bathing the instrument prior to surgery. When the glue seal is broken, the instrument becomes effectively unusable without significant repair.

Thus it is seen that an improved endoscopic adapter has been brought to the medical art. By employing an adapter that utilizes the principles and structures taught herein, the advantages offered by the coupling of endoscopic instruments with medical video equipment are maximized as image clarity is unhindered by the presence of condensation.

While this invention has been described with reference to its presently preferred embodiment, its scope is not limited thereto. Rather, such scope is limited only insofar as defined by the following set of claims and includes all equivalents thereof.

What is claimed is:

1. An adapter for coupling the proximal end of an endoscope to the head of a camera comprising, in combination;
   (a) a forward portion for engaging the proximal end of the endoscope;
   (b) a rearward portion for engaging the camera head, said rearward portion being arranged adjacent to said forward portion;
   (c) said forward and rearward portion being hollow throughout their entire axial lengths to define an inner aperture, for providing an unobstructed optical path between the camera head and the endoscope;
   (d) an optical window disposed inside said rearward portion of the adapter;
   (e) means for mounting fixedly said optical window inside said rearward portion, distally from the inner periphery of said rearward portion;
   (f) said means for mounting includes means for sealing said inner aperture around said optical window;
   (g) said sealing means being detachable and reusable; and
   (h) means for preventing substantially the occurrence of moisture condensation on the surface of said optical window, said means for preventing being detachable secured to said optical window.

2. An adapter as defined in claim 1 further characterized in that:
   (a) said window is of substantially round circumference;
   (b) said means for preventing comprises a plurality of heating elements; and
   (c) said elements are arranged about the periphery of said window whereby heat is radiated toward the center of said window.

3. An adapter as defined in claim 2 further including means for thermally insulating said window and said heating elements from the surrounding elements of said adapter.

4. An adapter as defined in claim 3 wherein said means for insulating comprises a cup-shaped element of elastomeric material.

5. An adapter as defined in claim 4 wherein said heating elements further include:
   (a) an annular printed circuit board positioned within said cup-shaped element; and
   (b) a plurality of surface mount resistors positioned in a wagon-train arrangement thereon.

6. An adapter as defined in claim 5 wherein said resistors are in electrical connection with the power supply of said camera.

7. An adapter as defined in claim 6 further characterized in that:
   (a) said adapter includes a chassis having an internal bore; and
   (b) said cup-shaped element is positioned within said bore.

8. An adapter as defined in claim 7 wherein said window is sealably secured to said chassis.

9. An adapter as defined in claim 1 wherein said means for mounting includes means for insulating thermally said optical window from the inner periphery of said rearward portion and from said forward portion.

10. An adapter as defined in claim 9 wherein said means for mounting includes:
    (a) an annular generally cup-shaped element for housing said optical window, and for sealing said inner aperture around said optical window; and
    (b) said annular element has an annular shoulder at its rearward end for providing a stop to retain said window inside said annular element.

11. An adapter as defined in claim 10 wherein said means for mounting further includes:
    (a) an annular ring for overlying said optical window;
    (b) said ring is complementary sized to fit inside, and to engage the inner periphery of said annular element; and
    (c) said ring includes a central opening of a smaller diameter than that of said optical window, to provide a stop for retaining it inside said annular element.

12. An adapter as defined in claim 11 wherein said annular element is made of suitable elastomeric material for insulating said optical window from the inner periphery of said rearward portion.

13. An adapter as defined in claim 12 wherein said means for insulating thermally includes:
    (a) an annular gasket disposed intermediate said optical window and said annular ring, for sealing said inner aperture around said optical window;
    (b) said gasket is made of suitable elastomeric material;
    (c) said gasket has a central opening of a smaller diameter than that of said optical window, for retaining it inside said annular element; and (d) said gasket is sized and dimensioned to engage the inner periphery of said annular element.

14. An adapter as defined in claim 10 wherein said means for preventing includes means for heating said optical window.

15. An adapter as defined in claim 14 wherein said means for heating includes a plurality of surface-mounted heating elements arranged about the periphery of said optical window, for causing heat to be radiated toward the center of said optical window, to clear the optical path through said inner aperture.

16. An adapter as defined in claim 15 wherein:
(a) said means for heating further includes an annular printed circuit board for connecting said heating elements in electrical communication; and
(b) said printed circuit board is mounted inside said annular element, and is disposed intermediate said heating elements and said annular shoulder of said annular element.

17. An adapter as defined in claim 16 wherein said means for heating further includes a pair of electrical conductors for supplying said printed circuit board with an electrical current.

18. An adapter as defined in claim 17 wherein said heating elements include a plurality of surface-mounted resistors positioned in a wagon-train arrangement on one surface of said optical window.

19. An adapter as defined in claim 1 further including a tubular hollow elongated focusing ring disposed intermediate said rearward portion and the camera head.

20. An adapter as defined in claim 19 further including viewing optics disposed inside said tubular focusing ring.

* * * * *